United States Patent
Young et al.

(10) Patent No.: US 7,063,705 B2
(45) Date of Patent: Jun. 20, 2006

(54) FLUOROSCOPIC LOCATOR AND REGISTRATION DEVICE

(75) Inventors: John Stewart Young, Memphis, TN (US); Harold S. Taylor, Memphis, TN (US); Tony Melkent, Memphis, TN (US); Thomas A. Carls, Memphis, TN (US); Chris Johnson, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 318 days.

(21) Appl. No.: 10/180,045

(22) Filed: Jun. 26, 2002

(65) Prior Publication Data

US 2003/0009169 A1   Jan. 9, 2003

Related U.S. Application Data

(60) Provisional application No. 60/302,499, filed on Jun. 29, 2001.

(51) Int. Cl.
*A61B 17/56* (2006.01)

(52) U.S. Cl. ...................................................... 606/86

(58) Field of Classification Search ............... 606/60, 606/61, 86, 90, 96, 97, 99, 102, 105, 130, 606/206, 207; 600/196, 201, 209, 210, 215, 600/219, 222, 225, 235, 407, 414, 417, 426, 600/427, 429

See application file for complete search history.

(56) References Cited

U.S. PATENT DOCUMENTS

| | | | |
|---|---|---|---|
| 832,201 A * | 10/1906 | Kistler | 604/108 |
| 3,486,505 A * | 12/1969 | Morrison | 606/90 |
| 3,941,127 A | 3/1976 | Froning | |
| 4,386,602 A | 6/1983 | Sheldon et al. | |
| 4,706,665 A * | 11/1987 | Gouda | 606/130 |
| 4,926,849 A * | 5/1990 | Downey | 602/34 |
| 5,047,036 A * | 9/1991 | Koutrouvelis | 606/130 |
| 5,080,662 A * | 1/1992 | Paul | 606/130 |
| 5,122,130 A * | 6/1992 | Keller | 606/61 |
| 5,176,129 A * | 1/1993 | Smith | 600/219 |
| 5,235,966 A * | 8/1993 | Jamner | 600/204 |
| 5,281,232 A | 1/1994 | Hamilton et al. | |
| 5,290,312 A * | 3/1994 | Kojimoto et al. | 623/17.15 |
| 5,383,454 A | 1/1995 | Bucholz | |
| 5,531,756 A | 7/1996 | Larose | |
| 5,630,431 A * | 5/1997 | Taylor | 128/897 |
| 5,665,122 A * | 9/1997 | Kambin | 623/17.16 |
| 5,697,889 A | 12/1997 | Slotman et al. | |
| 5,748,767 A * | 5/1998 | Raab | 382/128 |
| 5,749,362 A * | 5/1998 | Funda et al. | 600/407 |
| 5,772,594 A | 6/1998 | Barrick | |
| 5,868,675 A * | 2/1999 | Henrion et al. | 600/424 |
| 5,873,822 A | 2/1999 | Ferre et al. | |

(Continued)

FOREIGN PATENT DOCUMENTS

DE    200 04 812 U 1    9/2000

(Continued)

*Primary Examiner*—Eduardo C. Robert
*Assistant Examiner*—David Comstock
(74) *Attorney, Agent, or Firm*—Krieg Devault LLP

(57) ABSTRACT

A registration device is used to couple an identification superstructure of a surgical navigation system to the spinal column. The registration device includes a pair of vertebral engaging members positionable in a spinal disc space. At least one of the vertebrae engaging members moves outwardly from a collapsed position to engage the registration device to the endplates of the adjacent vertebrae.

30 Claims, 10 Drawing Sheets

U.S. PATENT DOCUMENTS

| | | | |
|---|---|---|---|
| 5,951,475 A | 9/1999 | Gueziec et al. | |
| 6,021,343 A | 2/2000 | Foley et al. | |
| 6,159,244 A * | 12/2000 | Suddaby | 623/17.11 |
| 6,167,292 A | 12/2000 | Badano et al. | |
| 6,190,414 B1 * | 2/2001 | Young et al. | 623/17.15 |
| 6,226,548 B1 | 5/2001 | Foley et al. | |
| 2002/0151894 A1 | 10/2002 | Melkent et al. | |

FOREIGN PATENT DOCUMENTS

| | | |
|---|---|---|
| EP | 0 950 379 A2 | 10/1999 |
| WO | WO94/24933 A1 | 11/1994 |
| WO | WO96/11624 A2 | 4/1996 |
| WO | WO96/11624 A3 | 4/1996 |

* cited by examiner

FLUOROSCOPIC LOCATOR AND REGISTRATION DEVICE

REFERENCE TO RELATED APPLICATION

The present application claims the benefit of U.S. Provisional Patent Application Ser. No. 60/302,499 filed Jun. 29, 2001 entitled "Fluoroscopic Locator and Registration Device" which is hereby incorporated by reference in its entirety.

BACKGROUND

The present invention generally relates to surgical navigation systems, and more specifically, but not exclusively, is directed to a device used for fluoroscopic registration of the spinal column.

Computer assisted image-guided medical and surgical navigation systems are known and used to generate images in order to guide doctors during surgical procedures. A number of different types of surgical navigation systems have been described that provide indications of position and/or orientation of patient anatomy, implants, and medical instruments during medical or surgical procedures. For example, U.S. Pat. No. 5,383,454 to Bucholz, PCT Application No. PCT/US94/04530 (Publication No. WO94/24933) to Bucholz, and PCT Application No. PCT/US95/12894 (Publication No. WO96/11624) to Bucholz et al., each of which is incorporated herein by reference in its entirety, disclose systems for use during surgical procedures using scans generated by a scanner prior to the procedure.

U.S. Pat. No. 6,226,548 to Foley et al., which is incorporated herein by reference in its entirety, discloses a percutaneous registration apparatus and computer assisted surgical navigation system for use during spinal surgery. In the '548 Foley patent, vertebral registration is achieved through a posterior incision and anchoring the identification superstructure to the spinous process. In one example, a surgeon inserts a screw and engages it to the spinous process, and attaches the identification superstructure to the screw. However, surgical navigation cannot begin until after the screw engaged to the vertebral body. In another example, a registration device is provided that includes a clamp engaged to the spinous process and the identification superstructure is attached to the registration device. Due to the irregular shape of the pedicles, securing the clamp to the pedicles can be difficult and therefore a rigid or secure connection can be difficult to obtain and maintain. Furthermore, registration from the spinous process requires an incision for each vertebral level that is to be registered.

There remains a need for methods and devices for registration of the spinal column that can be easily and securely affixed to the spinal column and also allow registration of more than one vertebral level.

SUMMARY

A registration device according to the present invention includes expandable vertebral engagement members that are adapted for insertion between adjacent vertebrae. When expanded, the registration device is secured to the adjacent endplates of the vertebrae.

One aspect of the present invention concerns a vertebral registration device. The device includes a connector adapted to connect an identification superstructure that is used for location identification during surgery. A vertebral engagement portion is coupled to the connector. The vertebral engagement portion is adapted to expand from a compact configuration to an expanded configuration in order to secure the vertebral engagement portion in a disc space between adjacent vertebrae. The vertebral engagement portion, when in the compact configuration, is able to fit into the disc space. When in the expanded configuration inside the disc space, the vertebral engagement portion engages the adjacent vertebrae.

Another aspect of the present invention concerns a vertebral registration device that includes a connector that is adapted to connect to a location identification superstructure. A vertebral engagement portion is coupled to the connector. The vertebral engagement portion is adapted to expand in a disc space between endplates of adjacent vertebrae and engage the endplates to secure the vertebral engagement portion to the vertebrae.

A further aspect of the present invention concerns a method of securing a registration device for fluoroscopic registration of a spinal column. The method includes inserting a vertebral engagement portion of a registration device between endplates of adjacent vertebrae in the spinal column. The vertebral engagement portion is expanded between the adjacent vertebrae to engage the vertebral engagement portion to the endplates.

Methods for fluoroscopic registration of the spinal column are also provided. The methods include securing a registration device to the spinal column and registering two levels of the spinal column with the one registration device.

Other forms, embodiments, objects, features, advantages, benefits and aspects of the present invention shall become apparent from the detailed drawings and description contained herein.

DETAILED DESCRIPTION

Figure 1:
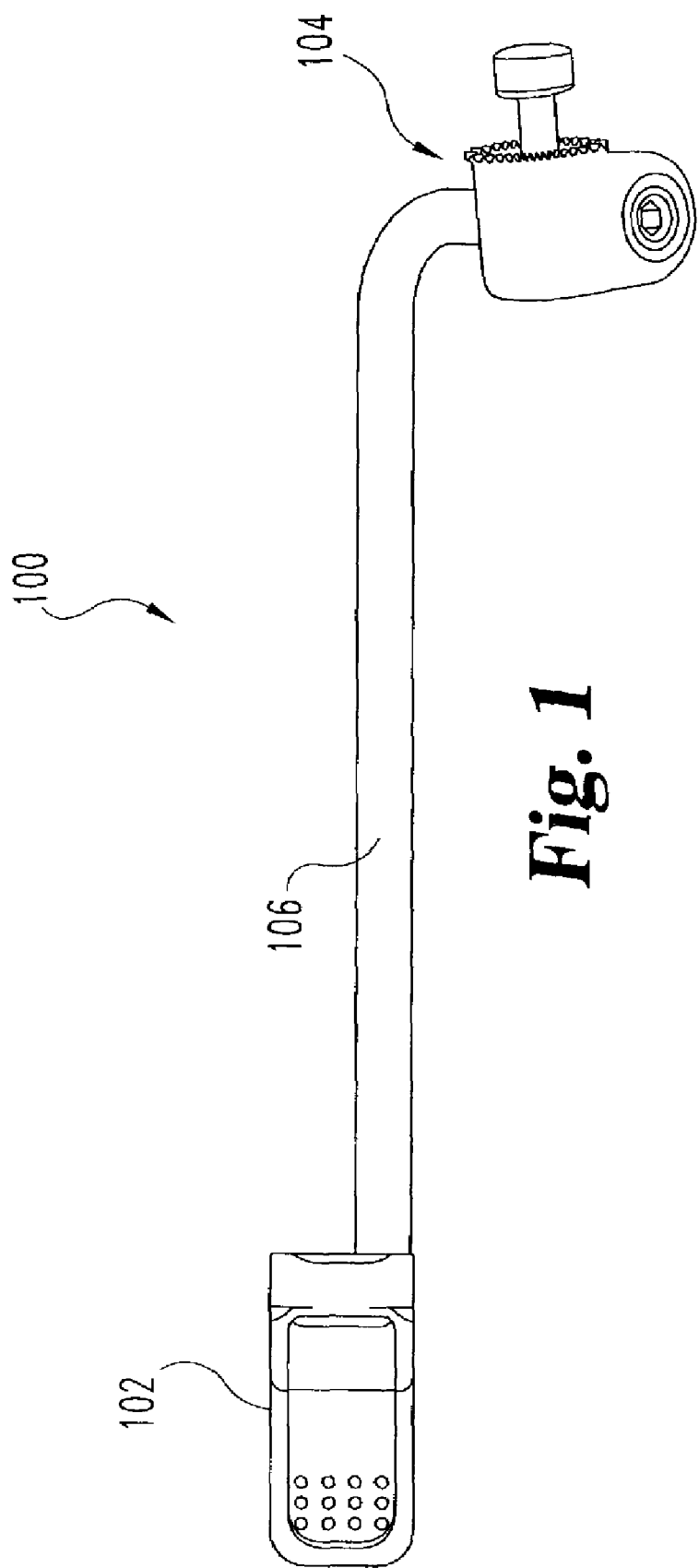
FIG. 1 is a top plan view of a registration device according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

It is believed that general operation of surgical navigation systems is well known in the art and therefore does not need to be described in detail herein. For example, U.S. Pat. No. 6,226,548 to Foley et al., which has been incorporated by reference in its entirety herein, provides a general description of one such type of system. Such systems typically employ an identification superstructure, such as a reference array that includes a plurality of emitters used by the navigation system in order to define a reference location for the surgical area. The reference array is used for determining the position and orientation of surgical instruments, implants, etc. during surgery. At the beginning of the surgery, the surgeon attaches a registration device to a known location along the spine and the identification superstructure is attached to the registration device, thus registering the identification superstructure to the patient anatomy. It is desirable that the registration device does not become dislodged or moved during the surgical procedure to prevent mis-registration.

A registration device 100 that can be attached to an identification superstructure, according to one embodiment of the present invention, is illustrated in FIG. 1. Registration device 100 includes a vertebral engagement portion 102, a connector 104 for attachment to the identification superstructure, and a shaft 106 extending between vertebral engagement portion 102 and connector 104. The vertebral engagement portion 102 secures registration device 100 to the spinal column segment. Connector 104 secures the identification superstructure (not shown) to registration device 100.

Figure 2:
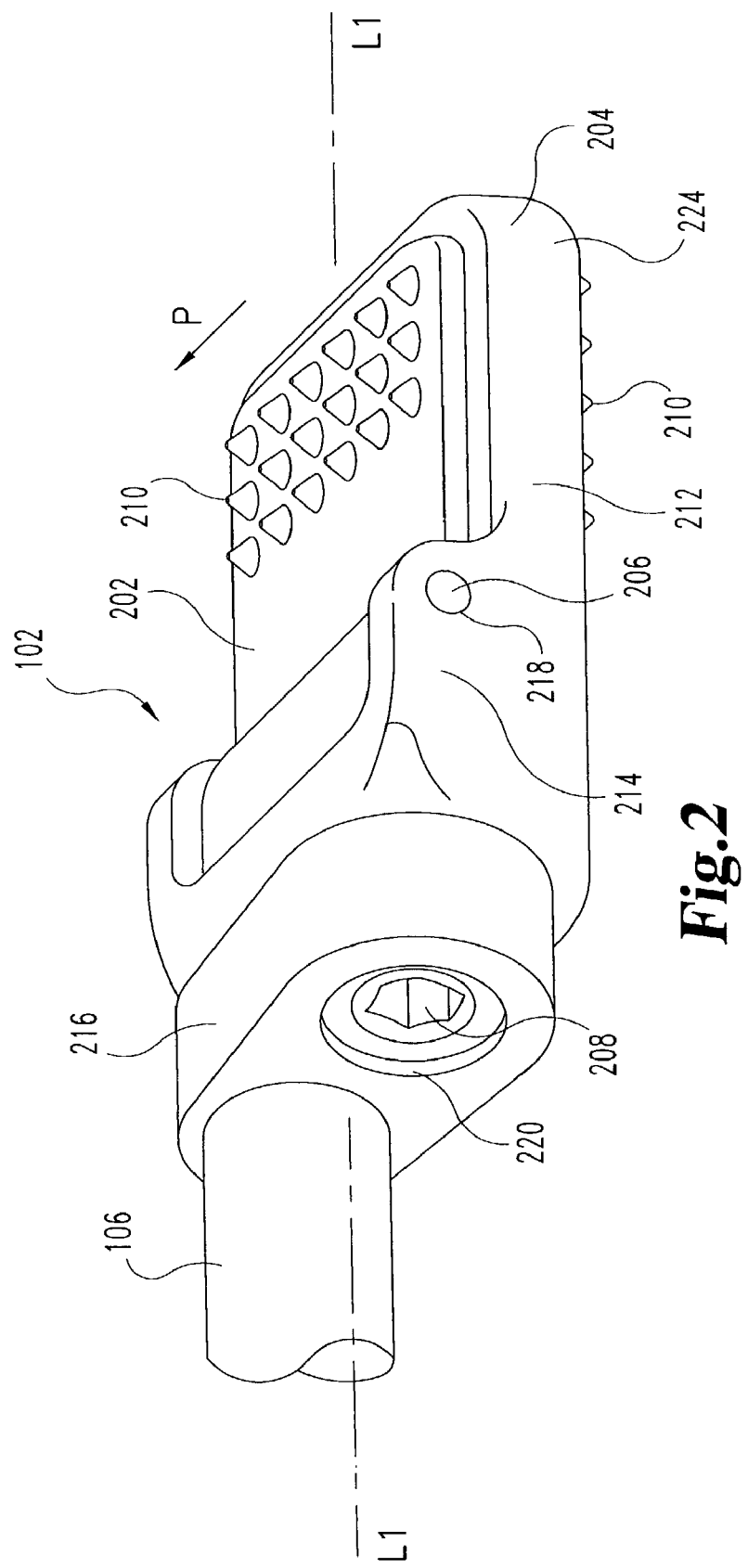
FIG. 2 is an enlarged perspective view of the distal end of the FIG. 1 registration device.

As shown further in FIG. 2, vertebral engagement portion 102 includes a first vertebral engaging member 202 pivotally attached to a second vertebral engagement member 204. Vertebral engagement portion 102 is inserted into the spinal disc space and engaged therein to secure registration device 100 to the spinal column. Vertebral engagement portion 102 has curved edges in order to minimize damage to tissue during surgery and insertion into the disc space. First member 202 is pivotally coupled to second member 204 through pivot pin 206. A driving member 208 in the form of a threaded screw is threadedly engaged in vertebral engagement portion 102 and can be threadingly advanced therein to pivot first member 202 relative to second member 204 about pin 206.

Vertebral engagement portion 102 engages adjacent vertebrae by pivoting first member 202 in direction P. As illustrated, second member 204 includes a base member 212 having a contact portion 224 along one side thereof which contacts one of the vertebral endplates. Second member 204 further includes a pivot portion 214 extending from base member 212 opposite contact portion 224. Pivot pin 206 pivotally attaches first member 202 to pivot portion 214 of second member 204. Pivot portion 214 includes a pin receiving opening 218 in which pin 206 resides. First member 202 and contact portion 224 each have teeth, knurlings, roughened surface or spikes 210 defined thereon that engage or embed in the endplate of the adjacent vertebra.

Adjacent pivot portion 214 vertebral engagement portion 102 has a connection portion 216. In the illustrated embodiment, connection portion 216 has a generally cylindrical/oval shape and includes a bore 220 in which driving member 208 is received. Bore 220 is offset to one side of a longitudinal axis L1 extending through the center of vertebral engagement portion 102. As shown, shaft 106 extends proximally from connection portion 216 and is offset from longitudinal axis L1 to the side opposite threaded bore 220.

Figure 3:
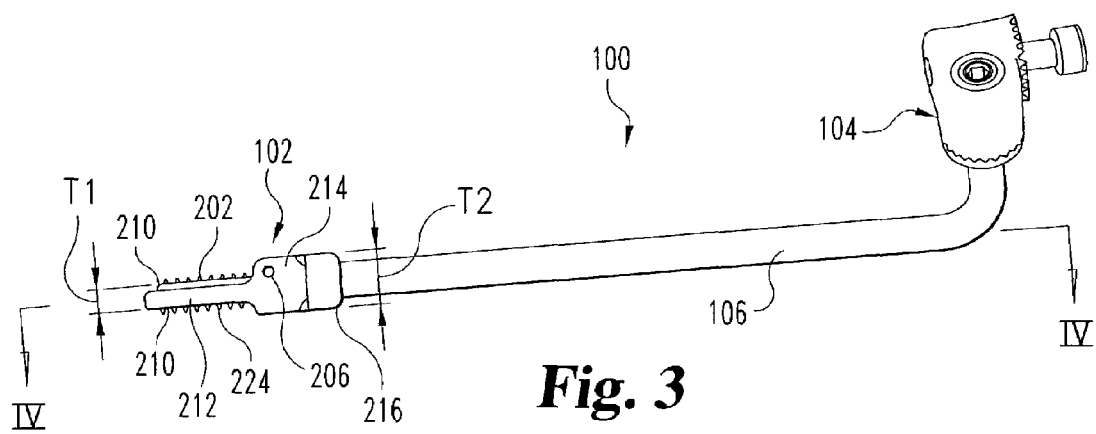
FIG. 3 is a side elevational view of the FIG. 1 registration device.
Figure 4:
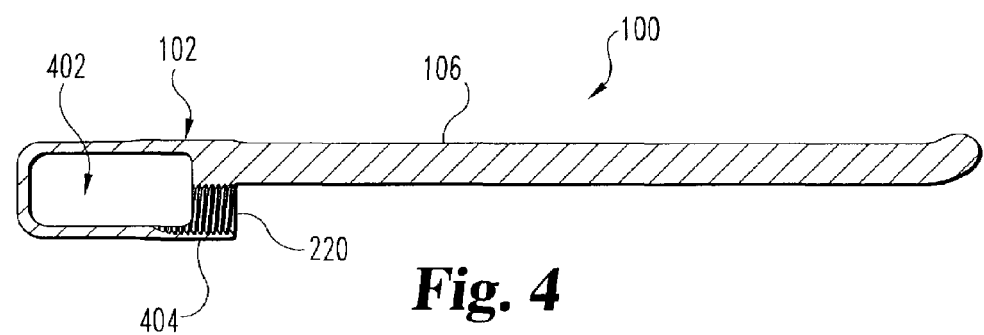
FIG. 4 is a cross-sectional view through line 4—4 of FIG. 3.

As illustrated in FIG. 3, vertebral engagement portion 102 has a thickness T1 at its distal end that is sized so that the vertebral engagement portion 102 can fit in the disc space between adjacent vertebrae. In FIG. 4, first member 202 has been removed, and base member 212 defines a receptacle 402 therein, which is sized to receive first member 202. First member 202 fits in pivot portion 214 of second member 204, and can be at least partially recessed in receptacle 402 in order to minimize thickness T1 of vertebral engagement portion 102. Bore 220 has threads 404, which are adapted to receive threads formed on driving member 208.

Figure 5:
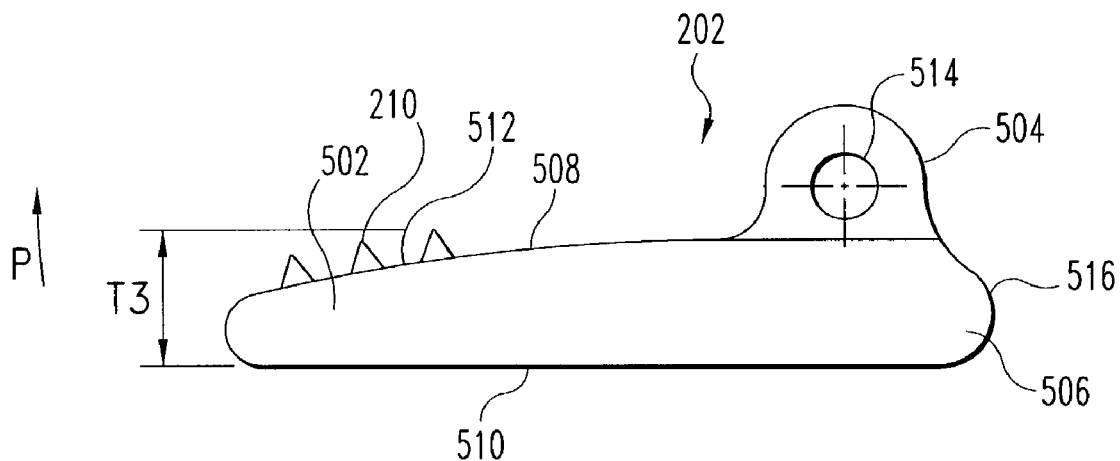
FIG. 5 is a side elevational view of a vertebral engaging member comprising a portion of the FIG. 1 registration device.
Figure 7:
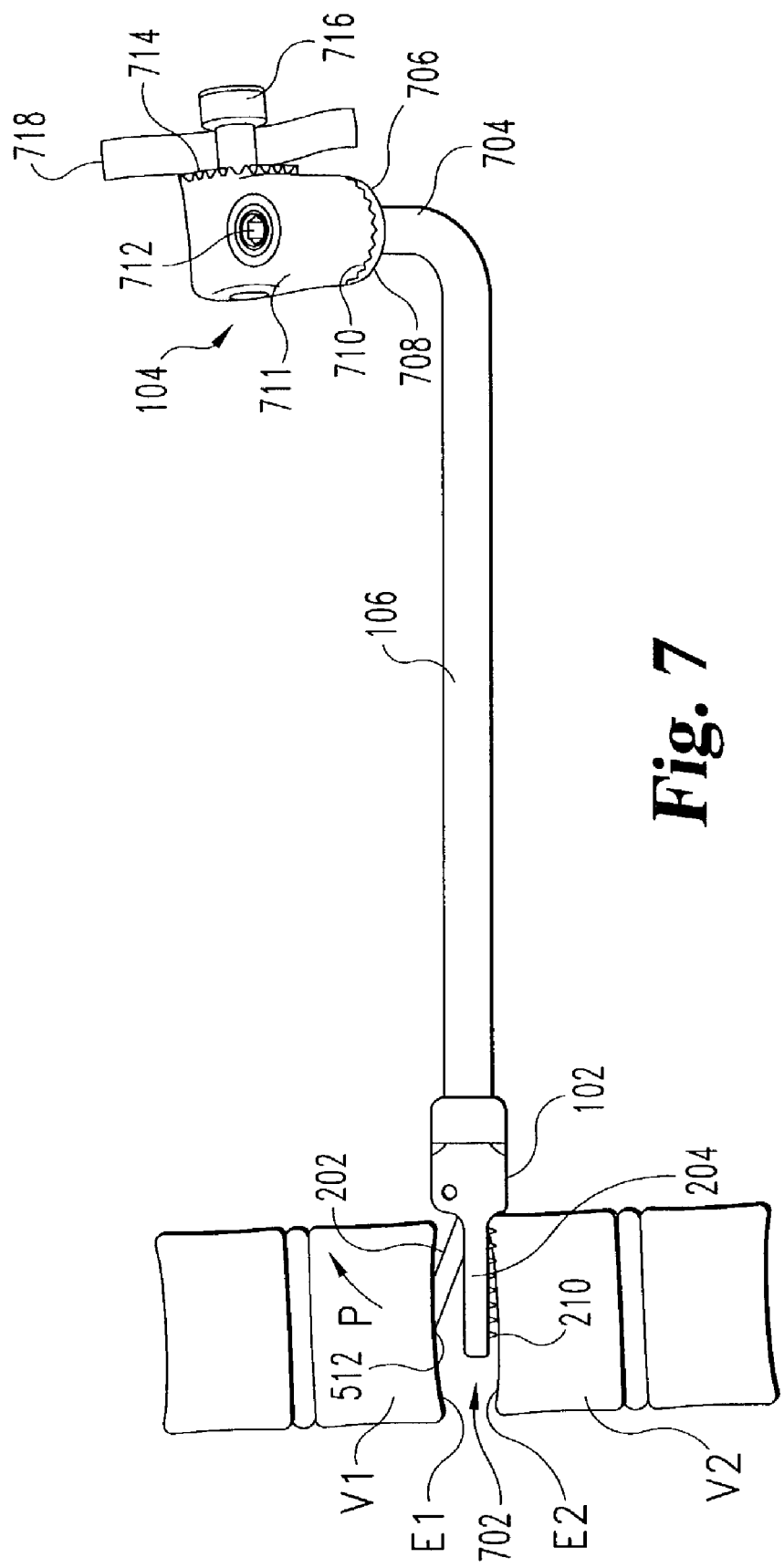
FIG. 7 is a side elevational view of the FIG. 1 registration device secured in a spinal disc space to adjacent vertebrae.

As shown in FIG. 5, first member 202 has a thickness T3, which in the illustrated embodiment is less than or equal to thickness T2 at the proximal end of vertebral engagement portion 102. First member 202 has a contact portion 502, a pivot arm 504, and a drive member engagement portion 506. Contact portion 502 includes a contact surface 508 and an oppositely disposed non-contact surface 510. Contact surface 508 can have a tapered/angled leading end surface 512 with spikes 210 extending therefrom. Leading end surface 512 is angled so that at least a portion of contact surface 508 remains in contact with the vertebral endplate when first member 202 is pivoted as shown in FIG. 7. Pivot portion 504 protrudes up from contact surface 508 and has a pin-receiving hole 514 defined therein. Pivot pin 206 is received in hole 514 to pivotally couple first member 202 to pivot portion 214 of second member 204. Drive member engagement portion 506 extends downwardly from pivot portion 514 to provide a contact surface for driving member 208 so that drive member 208 can pivot first member 202 in the direction of arrow P about pivot pin 206.

Figure 6:
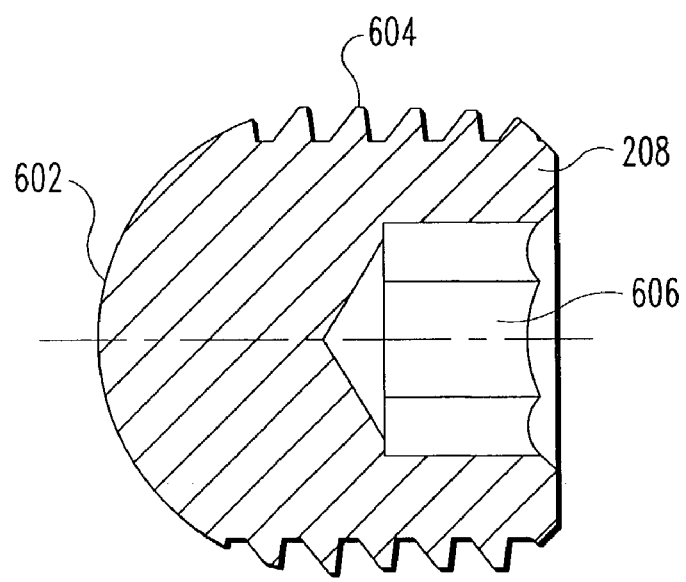
FIG. 6 is a cross-sectional view of a drive member comprising a portion of the FIG. 1 registration device.

As depicted in FIG. 6, driving member 208 includes a domed leading end 602, a threaded portion 604, and a tool engagement cavity 606 defined therein opposite leading end 602. Threads 604 are adapted to engage threads 404 of bore 220.

As shown in FIG. 7, vertebral engagement portion 102 is first inserted between adjacent vertebrae V1 and V2 in disc space 702. Driving member 208 is advanced in bore 220 to cause first member 202 to pivot in direction P, effecting expansion of vertebral engagement portion 102 and engagement of first member 202 and second member 204 to endplates E1 and E2 of vertebrae V1 and V2, respectively. Spikes 210 on each of first and second members 202, 204 engage end plates E1 and E2. Thus, registration device 100 is in contact with a vertebral element associated with two levels of the spinal column, and only a single incision in the patient is required in order to effect such multiple level registration.

Figure 8:
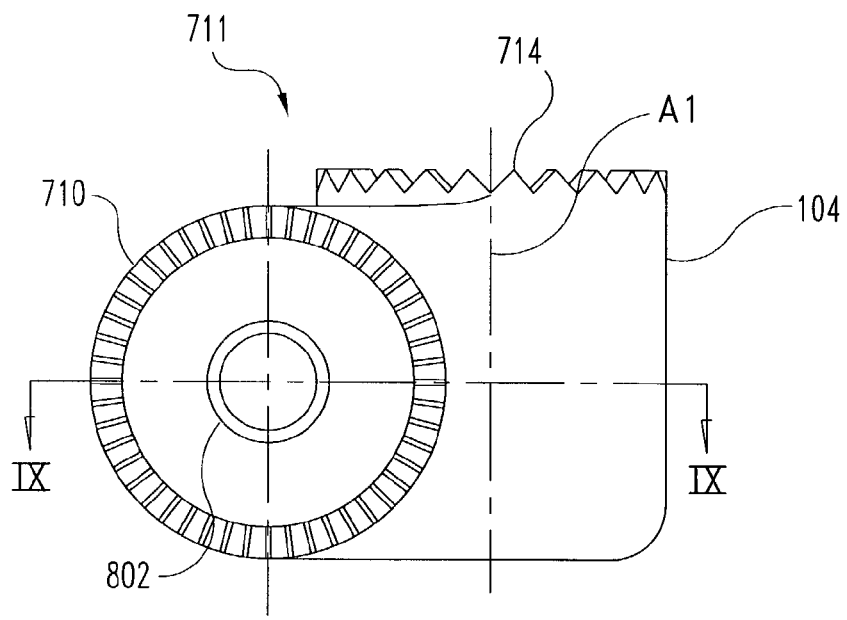
FIG. 8 is an elevational view of a coupling member comprising a portion of the FIG. 1 registration device.

Shaft 106 includes a bend 704 extending to connector 104. Connector 104 has an enlarged end 706 that includes a plurality of radially oriented ridges 708. As shown further in FIGS. 8 and 9, connector 104 further includes a coupling member 711 that has a plurality of radially oriented ridges 710 that are constructed and arranged to mate in interdigiting fashion with the ridges 708 on enlarged end 706. A fastener 712 secures coupling member 711 with enlarged end 706. As depicted in FIG. 8, ridges 710 are radially disposed around a hole 802 in which fastener 712 is received. As shown in greater detail in FIG. 9, hole 802 includes a threaded portion 902 and a counter sink portion 904 to eliminate protrusion of fastener 712. Fastener 712 can be loosened so that coupling member 711 can be rotated in order to reposition member coupling member 711 with respect to enlarged end 706 and then tightened in order to rigidly secure coupling member 711 thereto in a number of predetermined orientations defined by ridges 708, 710.

Figure 9:
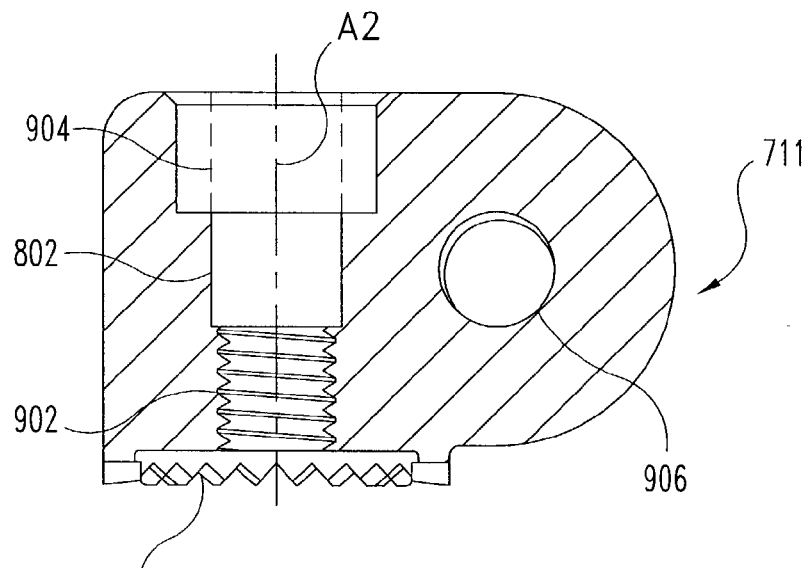
FIG. 9 is a cross-sectional view taken through line IX—IX of FIG. 8.

Coupling member 711 includes a second set of annularly disposed ridges 714, which are oriented around an axis A1 that is orthogonal to an axis A2 extending through hole 82. As shown in FIG. 9, hole 906 is formed in the center of ridges 714 receives a fastener 716 as shown in FIG. 7. An identification superstructure fastener 716 is used to secure the identification superstructure 718 to ridges 714 of coupling member 711 in interdigiting fashion. Identification superstructure 718 can thus be repositioned with respect to coupling member 711 and secured thereto in a number of predetermined orientations defined by ridges 714.

Figure 10:
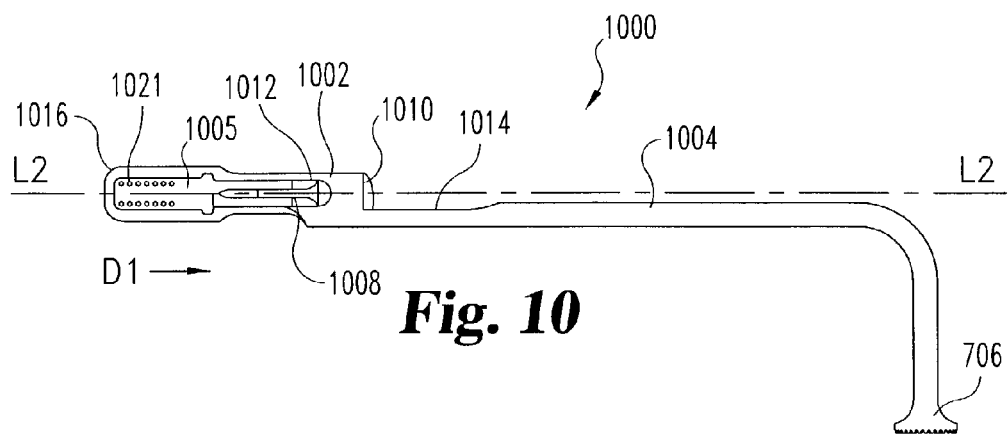
FIG. 10 is a top, plan view of a registration device according to another embodiment of the present invention.

A registration device 1000 according to another embodiment of the present invention will now be described with reference to FIGS. 10–18. As shown in FIG. 10, registration device 1000 includes a vertebral engagement portion 1002 connected to a shaft 1004 extending proximally to enlarged end 706. Vertebral engagement portion 1002 includes a first member 1005 and a second member 1006, a drive member 1008, an actuator 1010, a base member 1016, and a connection portion 1012. As shown, shaft 1004 is offset with respect to longitudinal axis L2 of registration device 1000. Shaft 1004 includes a recess portion 1014 proximal to actuator 1010 to facilitate surgeon access to actuator 1010 with a driving tool.

Figure 12:
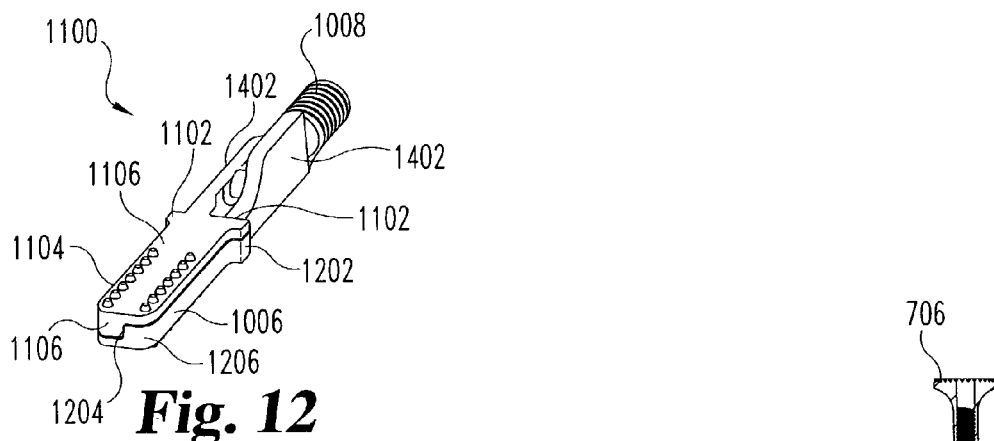
FIG. 12 is a perspective view of a subassembly comprising a portion of the FIG. 10 registration device.

In FIG. 12 there is shown a subassembly 100, which includes first and second members 1005, 1006 and drive member 1008 depicted in an unexpanded condition. First member 1005 includes alignment tabs 1102 and second member 1006 includes oppositely disposed alignment tabs 1202. In order to reduce the overall width of the first and second members 1004, 1005, and yet provide rigidity, each member 1005, 1006 has an engagement surface 1104, 1204 and a support rib 1106, 1206 extending therefrom toward one another, respectively. As shown, support ribs 1106, 1206 are offset with respect to one another so first and second members 1005, 1006 can be nested one on top of the other and reduce the overall thickness of the closed first and second members 1005, 1006.

Figure 13:
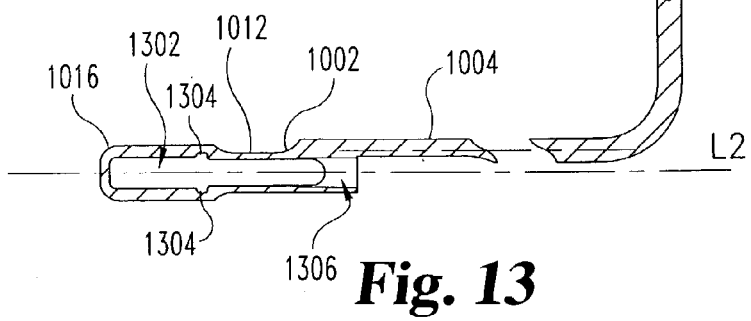
FIG. 13 is a cross-sectional view of a portion of the FIG. 10 registration device.

As illustrated in FIG. 13, vertebral engagement portion 1002 has a receptacle 1302 defined therein. Subassembly 1100 is adapted to fit within receptacle 1302. As depicted, receptacle 1302 includes a pair of oppositely disposed channels 1304 formed in base member 1016 that are constructed to receive alignment tabs 1102, 1202 on first and second members 1005, 1006, respectively. Connection portion 1012 further has a bore 1306 in which drive member 1008 is received.

Figure 14:
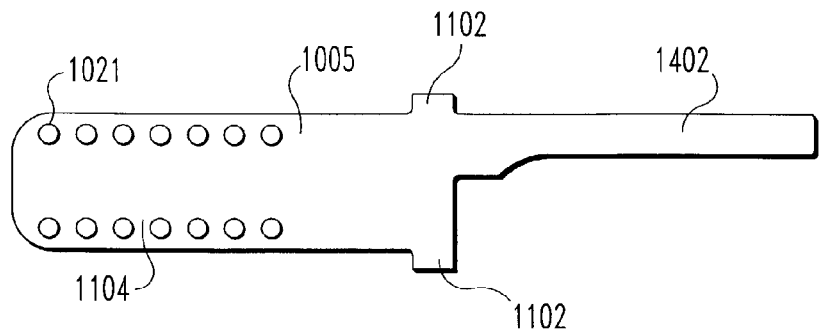
FIG. 14 is a top, plan view of a vertebral engaging member comprising a portion of the FIG. 10 registration device.
Figure 15:
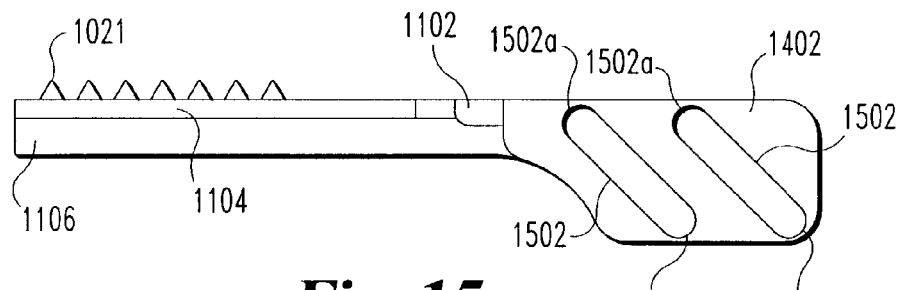
FIG. 15 is a side elevational view of the FIG. 14 vertebral engaging member.

First member 1005 will now be described with reference to FIGS. 14 and 15, it being understood that second member 1006 is identical but oriented such that its spikes 1021 face in the direction opposite spikes 1021 of first member 1005 when assembled thereto as shown in FIG. 13. First member 1005 has a drive member engaging portion 1402 constructed to engage drive member 1008. As shown, a pair of angled slots 1502 are defined in drive member engaging portion 1402, and the slots 1502 extend in a parallel relationship with one another. Slots 1502 are angled to form a distal end 1502a and a proximal end 1502b.

Figure 16:
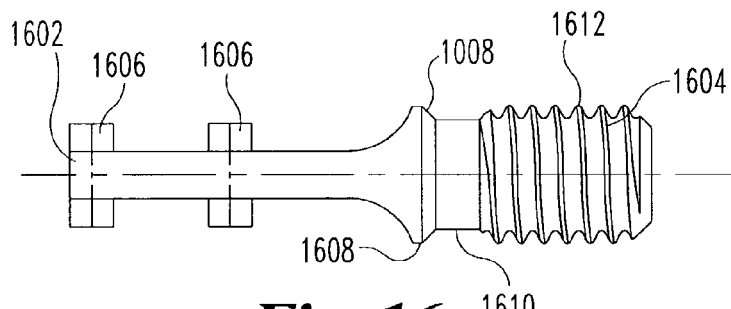
FIG. 16 a top plan view of a drive member comprising a portion of the FIG. 10 registration device.
Figure 17:
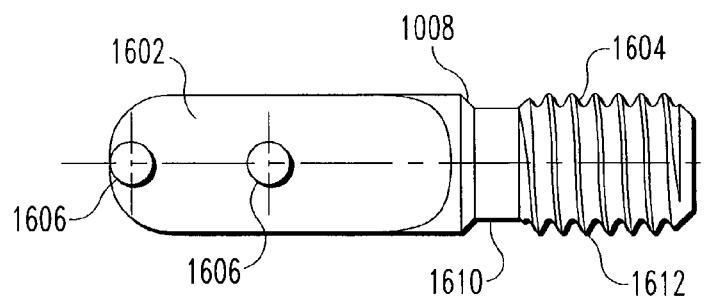
FIG. 17 is a side view of the FIG. 16 drive member.

Drive member 1008 is illustrated in further detail in FIGS. 16–17. As shown, drive member 1008 has driving end portion 1602 and a threaded portion 1604. Driving end portion 1602 has a pair of slot engagement rods 1606 extending therethrough and extending from each side thereof. Slot engagement rods 1606 are adapted to each mate with a corresponding one of the slots 1502 in first and second members 1005, 1006. The driving end portion 1602 has a relatively thin cross-sectional shape in order to fit between the drive member engaging portions 1402 of first and second members 1005, 1006 when first and second members 1005, 1006 are positioned as shown in FIG. 12. A beveled connection portion 1608 connects driving end portion 1602 to threaded portion 1604 through an unthreaded intermediate portion 1610. Threaded portion 1604 has threads 1612 that engage actuator 1010 when registration device 1000 is assembled as shown in FIG. 1.

Figure 18:
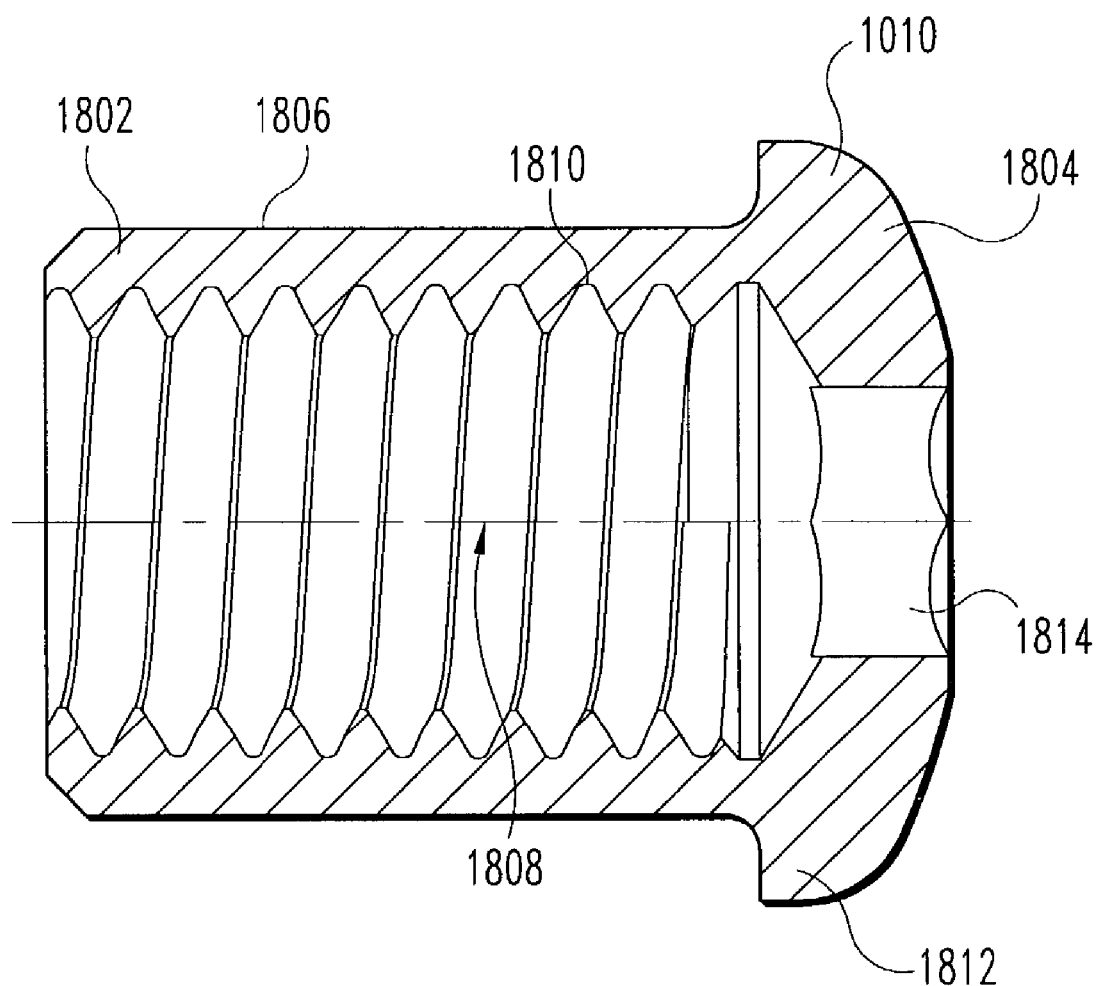
FIG. 18 is a cross-sectional view through the longitudinal axis of an actuator comprising a portion of the FIG. 10 registration device.

As depicted in FIG. 18, actuator 1010 includes a drive member coupler 1802 and a head 1804. Drive member coupler 1802 has a smooth exterior surface 1806 to rotate in bore 1306 and a threaded interior cavity 1808. Cavity 1808 has threads 1810 that are adapted to engage threads 1612 of drive member 1008. Head 1804 is sized larger than drive member coupler 1802 and has a flange portion 1812 adapted to bear against the connection portion 1012 around bore 1306. Head 1804 further includes a tool receiving cavity 1814 that is adapted to receive a driving tool.

Figure 11:
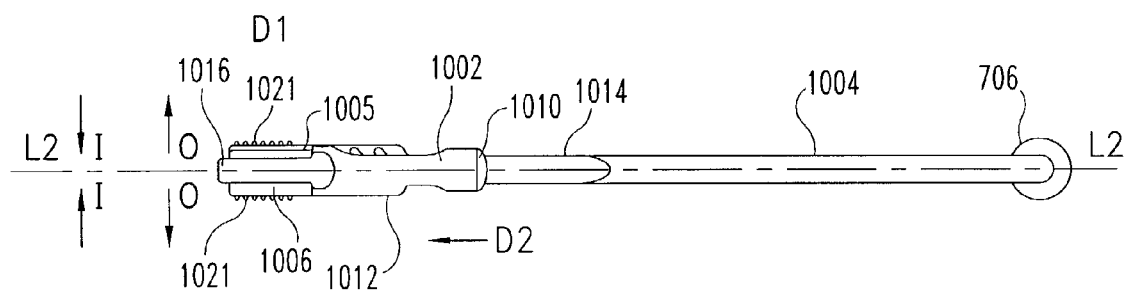
FIG. 11 is a side elevational view of the FIG. 10 registration device.

Referring to FIG. 11, operation of registration device will be described. Turning actuator 1010 in a first direction pulls drive member 1008 in direction D1, causing rod 1606 to move from distal end 1502a of slots 1502 to proximal end 1502b. This in turn, as shown in FIG. 11, causes the first and second members 1005, 1006 to move or expand in an outward direction O with respect to longitudinal axis L2. At the expanded position, spikes 1021 defined on the first and second members 1005, 1006 engage the end plates E1 and E2 in order to secure the registration device 1000 tightly to the vertebrae V1 and V2. To disengage the registration device 1000, actuator 1010 is rotated in an opposite direction so as to push drive member 1008 in direction D2 opposite D1. Movement of drive member 1008 in direction D2 causes rods 1606 to move from proximal end 1502b of slots 1502 to distal end 1502a, thereby directing first and second members 1005, 1006 to move in inward direction I so as to disengage from the endplates of vertebrae V1 and V2.

Figure 19:
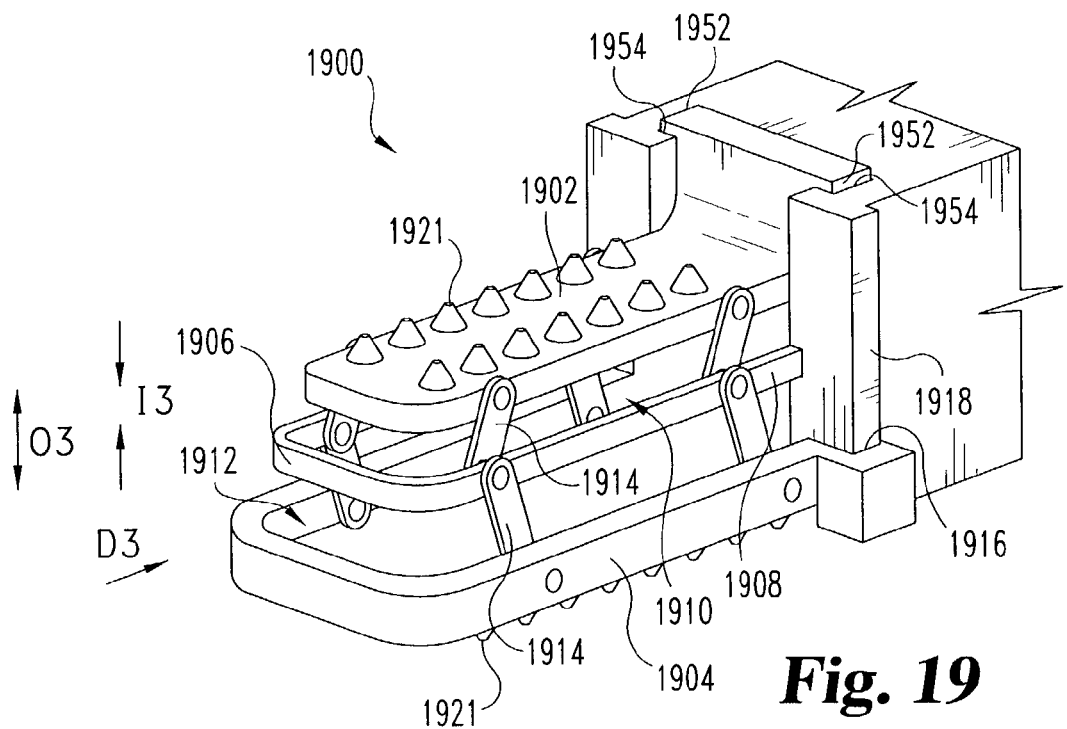
FIG. 19 is a perspective view of a further embodiment vertebral engagement portion comprising a portion of the registration device of the present invention.

Another embodiment vertebral engagement portion 1900 for use with the registration devices of the present invention is illustrated in FIG. 19. Vertebral engagement portion 1900 has an inner first member 1902 and an outer second member 1904. First and second members 1902, 1904 have spikes 1921 defined thereon. First member 1902 has a pair of alignment tabs 1952 that are received in alignment slots 1954 formed in vertebral engagement portion 1900. Second member 1904 includes a channel 1916 into which a rail 1918 of vertebral engagement portion 1900 is slidably received. A drive member 1906 is slidably received into slots 1908 formed in vertebral engagement portion 1900 extending parallel to the longitudinal axis of the registration device, and is movable both in the direction of and the opposite direction of arrow D3. Drive member 1906 has an inner receptacle 1910 in which first member 1902 is received. In a similar manner, second member 1904 has a second receptacle 1912 defined therein to receive both first member 1902 and drive member 1906 when first and second members 1902, 1904 are collapsed about drive member 1906.

Linkages 1914 pivotally link drive member 1906 to first member 1902 and second member 1904. When the drive member 1906 is moved in direction D3 by an actuator (not shown), the vertebral engagement portion 1900 expands with first and second members 1902, 1904 pivoting about links 1914 and moving in an outward direction O3. During this expansion movement, first member 1902 moves upwardly in slots 1954 and second member 1904 moves downwardly along rails 1918. By moving driving member 1906 in the opposite direction of D3, the first and second members pivot about links 1914 in an inward direction I3 and into a collapsed configuration in which first member 1902 is nested within drive member 1906 and a second member 1904 is positioned about drive member 1906. It is further contemplated that movement of drive member 1906 in the direction of D3 could collapse first and second members 1902, 1904, and movement of drive member 1906 in the direction opposite D3 could expand first and second members 1902, 1904.

Figure 20:
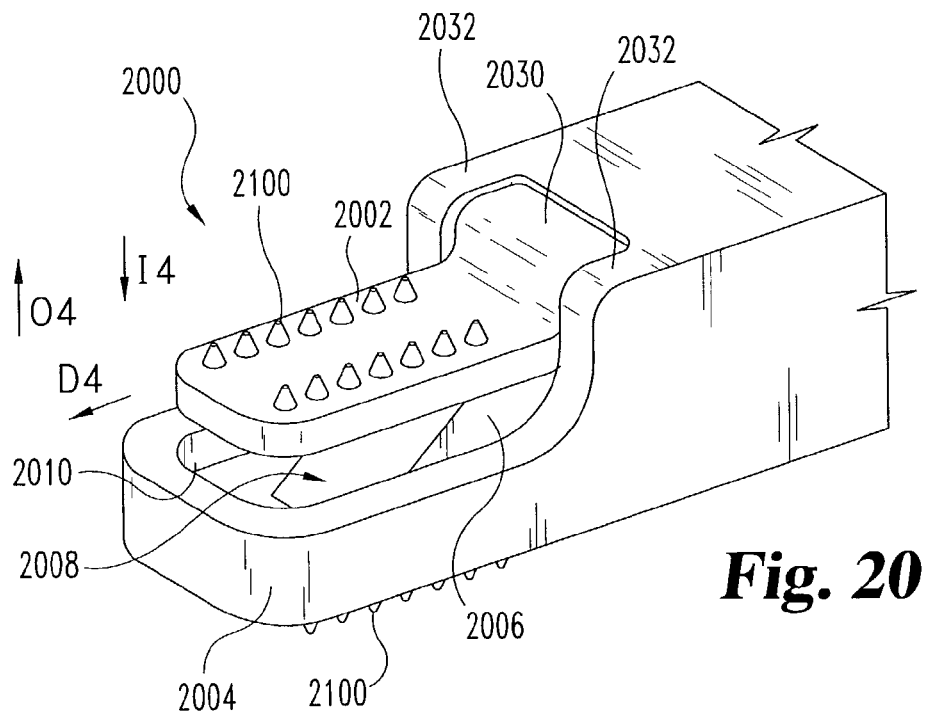
FIG. 20 is a perspective view another embodiment vertebral engagement portion comprising a portion of the registration device of the present invention.

A vertebral engagement portion 2000 according to another embodiment of the present invention is illustrated in FIG. 20. Vertebral engagement portion 2000 includes a moveable first member 2002 that has spikes 2100 defined thereon, a fixed second member 2004 that also includes spikes 2100, and a drive member 2006. First member 2002 has flanges 2030 extending from a proximal end thereof which are received into slots 2032 formed in vertebral engagement portion 2000. Drive member 2006 has a ramp or wedge shaped surface 2008 that engages the bottom side of first member 2002. Second member 2004 defines a receptacle 2010 in which drive member 2006 is slidably received. In order to expand first member 2002 in outward direction O4, drive member 2006 is moved in direction D4. Ramp surface 2008 engages first member 2002 and pushes it in outward direction O4 so that teeth 2100 engage the vertebral endplates. By moving drive member 2006 in the direction opposite D4, first member 2002 moves in an inward direction 14 to a retracted position for withdrawal or insertion into the disc space.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A vertebral registration device, comprising:
   a connector adapted to connect to an identification superstructure that is used for location identification during surgery; and
   a vertebral engagement portion coupled to the connector, the vertebral engagement portion being adapted to expand from a compact configuration to an expanded configuration to secure the vertebral engagement portion in a disc space between adjacent vertebrae, the vertebral engagement portion when in the compact configuration being able to fit into the disc space, the vertebral engagement portion when in the expanded configuration inside the disc space engages the adjacent vertebrae;
   wherein the connector includes
      an enlarged end portion having a plurality of radially oriented ridges,
      a coupling member defining a first hole extending along a first axis, the coupling member having a first set of ridges radially oriented around the first hole,
      a fastener received in the first hole to mate the first set of ridges of the coupling member with the ridges on the enlarged end portion in an interdigiting fashion and to allow rotational repositioning the coupling member relative to the enlarged end portion, and
      the coupling member defining a second hole extending along a second axis that is orthogonal to the first axis, the coupling member having a second set of ridges radially oriented around the second hole, the second set of ridges being constructed and arranged to mate in an interdigiting fashion with ridges on the identification superstructure.

2. The device of claim 1, wherein the vertebral engagement portion includes:
   a first member;
   a second member, the first member being pivotally connected to the second member; and
   a drive member positioned proximal the first member to pivot the first member to the expanded configuration.

3. The device of claim 2, wherein:
   the second member defines a receptacle sized to receive the first member;
   the first member is at least partially received within the receptacle when the vertebral engagement portion is in the compact configuration.

4. The device of claim 3, wherein the first member has a tapered leading edge.

5. The device of claim 2, wherein both the first member and the second member have spikes adapted to engage the vertebrae.

6. The device of claim 1, further comprising a shaft connecting the vertebral engagement portion to the connector.

7. The device of claim 6, wherein the shaft includes a bend portion proximal the connector.

8. The device of claim 1, wherein the vertebral engagement portion includes:
   a drive member;
   a first member having a first drive engaging portion engaging the drive member;
   a second member oriented in an opposing relationship with the first member, the second member having a second drive engaging portion engaging the drive member; and
   wherein the drive member is adapted to drive the first member and the second member apart from one another to the expanded configuration.

9. The device of claim 8, wherein:
   the first member has a first vertebrae engagement surface and a first support rib extending from the first vertebrae engagement surface towards the second member;

the second member has a second vertebrae engagement surface and a second support rib extending from the second vertebrae engagement surface towards the first member; and the first support rib of the first member and the second support rib of the second member are offset with respect to one another to nest together in the compact configuration.

10. The device of claim 8, wherein:

the first drive engaging portion of the first member defines a first pair of angled slots;

the second drive engaging portion of the second member defines a second pair of angled slots; and the drive member has a driving end portion received between the first drive engaging portion and the second drive engaging portion, the driving end portion having a slot engagement rods engaging the first pair of angled slots and the second pair of angled slots.

11. The device of claim 8, wherein the vertebral engagement portion defines a receptacle in which at least a portion of the first member and the second member are received in the compact configuration.

12. The device of claim 11, wherein:

the vertebral engagement portion defines a pair of oppositely disposed channels;

the first member has a first pair of opposing alignment tabs received in the oppositely disposed channels in the vertebral engagement portion; and the second member has a second pair of opposing alignment tabs received in the oppositely disposed channels in the vertebral engagement portion.

13. The device of claim 8, further comprising an actuator coupled to the drive member to move the drive member.

14. The device of claim 13, wherein:

the vertebral engagement portion defines a bore in which the actuator is received;

the drive member has a threaded portion;

the actuator defines a tool receiving cavity adapted to receive a driving tool; and the actuator has a smooth exterior surface to rotate in the bore and a threaded interior cavity engaged with the threaded portion of the drive member.

15. The device of claim 13, further comprising a shaft connecting the vertebral engagement portion to the connector, the shaft being offset with respect to a longitudinal axis of the vertebral engagement portion, wherein the shaft defines a recess portion proximal the actuator to facilitate access of the driving tool.

16. The device of claim 8, wherein the first member and the second member each have vertebrae engagement spikes.

17. The device of claim 16, further comprising:

an actuator coupled to the drive member to move the drive member;

the vertebral engagement portion defining a bore in which the actuator is received;

the drive member having a threaded portion;

the actuator defining a tool receiving cavity adapted to receive a driving tool;

the actuator having a smooth exterior surface to rotate in the bore and a threaded interior cavity engaged with the threaded portion of the drive member;

a shaft connecting the vertebral engagement portion to the connector, the shaft being offset with respect to a longitudinal axis of the vertebral engagement portion, wherein the shaft defines a recess portion proximal the actuator to facilitate access of the driving tool;

the first member having a first vertebrae engagement surface and a first support rib extending from the first vertebrae engagement surface towards the second member;

the second member having a second vertebrae engagement surface and a second support rib extending from the second vertebrae engagement surface towards the first member;

the first support rib of the first member and the second support rib of the second member being offset with respect to one another to nest together in the compact configuration;

the first drive engaging portion of the first member defining a first pair of angled slots;

the second drive engaging portion of the second member defining a second pair of angled slots;

the drive member having driving end portion received between the first device engaging portion and the second drive engaging portion, the driving end portion having a slot engagement rods engaging the first pair of angled slots and the second pair of angled slots;

the vertebral engagement portion defining a receptacle in which at least a portion of the first member and the second member are received in the compact configuration;

the vertebral engagement portion defining a pair of oppositely disposed channels;

the first member having a first pair of opposing alignment tabs received in the oppositely disposed channels in the vertebral engagement portion; and the second member having a second pair of opposing alignment tabs received in the oppositely disposed channels in the vertebral engagement portion.

18. The device of claim 1, wherein:

the vertebral engagement portion includes a first member, a second member, a drive member, and linkages pivotally connecting the first member and the second member to the drive member;

the vertebral engagement portion defines an alignment slot and a drive slot;

the vertebral engagement portion has a rail;

the first member has an alignment tab slidably received in the alignment slot;

the second member defines a channel in which the rail is received; and the drive member is slidably received in the drive slot to drive the first member and the second member apart to the expanded configuration through the linkages.

19. The device of claim 18, wherein:

the drive member defines a first receptacle configured to receive the first member when the vertebral engagement portion is in the compact configuration; and the second member defines a second receptacle configured to receive the drive member and the first member when the vertebral engagement portion is in the compact configuration.

20. The device of claim 1, wherein:

the vertebral engagement portion defines slots;

the vertebral engagement portion includes a moveable first member having flanges slidably received in the slots;

a fixed second member defining a drive cavity; and a drive member slidably received in the drive cavity, the drive member having a ramp shaped surface contacting the first member to drive first member away from the second member to the expanded configuration.

21. The device of claim 20, wherein the second member defines a receptacle configured to slidably receive the first member.

22. The device of claim 1, further comprising the identification superstructure connected to the connector.

23. A method of securing a registration device for fluoroscopic registration of a spinal column, comprising:
inserting a vertebral engagement portion of the registration device between endplates of adjacent vertebrae in the spinal column;
expanding the vertebral engagement portion between the adjacent vertebrae to engage the vertebral engagement portion with the endplates;
wherein said expanding includes sliding a moveable first member in the registration device away from a fixed second member in the registration device; and
coupling a location identification superstructure to a connector on the registration device.

24. The method of claim 23 wherein the first member is pivotally coupled to the second member.

25. The method of claim 24, wherein the first member is pivotally coupled to the second member at a location adjacent the connector and the first and second members extend from the location away from the connector.

26. A vertebral registration device, comprising:
a connector adapted to connect to an identification superstructure that is used for location identification during surgery; and
a vertebral engagement portion coupled to the connector, the vertebral engagement portion being adapted to expand from a compact configuration to an expanded configuration to secure the vertebral engagement portion in a disc space between adjacent vertebrae, the vertebral engagement portion when in the compact configuration being able to fit into the disc space, the vertebral engagement portion when in the expanded configuration inside the disc space engages the adjacent vertebrae, wherein the vertebral engagement portion comprises:
a first member;
a second member, the first member being pivotally connected to the second member;
a drive member positioned proximal the first member to pivot the first member to the expanded configuration,
wherein the second member defines a receptacle sized to receive the first member; and
wherein the first member is at least partially received within the receptacle when the vertebral engagement portion is in the compact configuration.

27. The device of claim 26, wherein the first member has a tapered leading edge.

28. A vertebral registration device, comprising:
a connector adapted to connect to an identification superstructure that is used for location identification during surgery;
a vertebral engagement portion coupled to the connector, the vertebral engagement portion being adapted to expand from a compact configuration to an expanded configuration to secure the vertebral engagement portion in a disc space between adjacent vertebrae, the vertebral engagement portion when in the compact configuration being able to fit into the disc space, the vertebral engagement portion when in the expanded configuration inside the disc space engages the adjacent vertebrae; and
a shaft connecting the vertebral engagement portion to the connector, wherein the shaft includes a bend portion proximal the connector.

29. A vertebral registration device, comprising:
a connector adapted to connect to an identification superstructure that is used for location identification during surgery;
a vertebral engagement portion coupled to the connector, the vertebral engagement portion being adapted to expand from a compact configuration to an expanded configuration to secure the vertebral engagement portion in a disc space between adjacent vertebrae, the vertebral engagement portion when in the compact configuration being able to fit into the disc space, the vertebral engagement portion when in the expanded configuration inside the disc space engages the adjacent vertebrae;
wherein the vertebral engagement portion defines slots;
wherein the vertebral engagement portion includes a moveable first member having flanges slidably received in the slots;
a fixed second member defining a drive cavity; and
a drive member slidably received in the drive cavity, the drive member having a ramp shaped surface contacting the first member to drive first member away from the second member to the expanded configuration.

30. The device of claim 29, wherein the second member defines a receptacle configured to slidably receive the first member.

* * * * *